(12) United States Patent
Naveh

(10) Patent No.: US 12,728,263 B2
(45) Date of Patent: Sep. 8, 2026

(54) DELIVERING TUMOR TREATING FIELDS (TTFields) TO THE NECK, THORACIC SPINE, AND OPTIC TRACT

(71) Applicant: Novocure GmbH, Root (CH)

(72) Inventor: Ariel Naveh, Haifa (IL)

(73) Assignee: Novocure GmbH, Baar (CH)

( * ) Notice: Subject to any disclaimer, the term of this patent is extended or adjusted under 35 U.S.C. 154(b) by 106 days.

(21) Appl. No.: 18/944,922

(22) Filed: Nov. 12, 2024

(65) Prior Publication Data

US 2025/0161671 A1 May 22, 2025

Related U.S. Application Data

(60) Provisional application No. 63/600,338, filed on Nov. 17, 2023.

(51) Int. Cl.

*A61N 1/36* (2006.01)
*A61N 1/04* (2006.01)
*A61N 1/32* (2006.01)
*A61N 1/40* (2006.01)

(52) U.S. Cl.

CPC ....... *A61N 1/36002* (2017.08); *A61N 1/0408* (2013.01); *A61N 1/323* (2013.01); *A61N 1/36034* (2017.08)

(58) Field of Classification Search

CPC .. A61N 1/0408; A61N 1/0416; A61N 1/0476; A61N 1/323; A61N 1/36002; A61N 1/36034; A61N 1/40

USPC ........................................ 607/1–95, 115–156

See application file for complete search history.

(56) References Cited

U.S. PATENT DOCUMENTS

| | | | |
|---|---|---|---|
| 6,868,289 | B2 | 3/2005 | Palti |
| 7,016,725 | B2 | 3/2006 | Palti |
| 7,089,054 | B2 | 8/2006 | Palti |
| 7,136,699 | B2 | 11/2006 | Palti |
| 7,333,852 | B2 | 2/2008 | Palti |
| 7,467,011 | B2 | 12/2008 | Palti |
| 7,519,420 | B2 | 4/2009 | Palti |
| 7,565,205 | B2 | 7/2009 | Palti |
| 7,565,206 | B2 | 7/2009 | Palti |

(Continued)

OTHER PUBLICATIONS

International Search Report and Written Opinion issued in application No. PCT/IB2024/061249 dated Jan. 31, 2025.

*Primary Examiner* — Benjamin J Klein
*Assistant Examiner* — Vynn V Huh
(74) *Attorney, Agent, or Firm* — Potomac Law Group, PLLC

(57) ABSTRACT

During Tumor Treating Fields (TTFields) therapy, one or more pairs of electrode assemblies are used to impose an alternating electric field to the tumor. However, when the cancer cells are distributed among two or more different locations within the subject's body, it can be difficult to achieve sufficient field intensities in all of the different locations. By positioning one pair of electrode assemblies on the left half of the subject's scalp and the right side of the subject's posterior thorax, and positioning another pair of electrode assemblies on the right half of the subject's scalp and the left side of the subject's posterior thorax, it becomes possible to achieve sufficient field intensities in the following three locations simultaneously: (i) an upper half of the subject's thoracic spine, (ii) the subject's cervical spine, and (iii) the subject's head.

16 Claims, 2 Drawing Sheets

(56) References Cited

U.S. PATENT DOCUMENTS 7,599,745 B2 10/2009 Palti
7,599,746 B2 10/2009 Palti
7,706,890 B2 4/2010 Palti
7,715,921 B2 5/2010 Palti
7,805,201 B2 9/2010 Palti
7,890,183 B2 2/2011 Palti et al.
7,912,540 B2 3/2011 Palti
7,917,227 B2 3/2011 Palti
8,019,414 B2 9/2011 Palti
8,027,738 B2 9/2011 Palti
8,170,684 B2 5/2012 Palti
8,175,698 B2 5/2012 Palti et al.
8,229,555 B2 7/2012 Palti
RE43,618 E 8/2012 Palti
8,244,345 B2 8/2012 Palti
8,406,870 B2 3/2013 Palti
8,447,395 B2 5/2013 Palti et al.
8,447,396 B2 5/2013 Palti et al.
8,465,533 B2 6/2013 Palti
8,706,261 B2 4/2014 Palti
8,715,203 B2 5/2014 Palti
8,718,756 B2 5/2014 Palti
8,764,675 B2 7/2014 Palti
9,023,090 B2 5/2015 Palti
9,023,091 B2 5/2015 Palti
9,039,674 B2 5/2015 Palti et al.
9,056,203 B2 6/2015 Palti et al.
9,440,068 B2 9/2016 Palti et al.
9,655,669 B2 5/2017 Palti et al.
9,750,934 B2 9/2017 Palti et al.
9,910,453 B2 3/2018 Wasserman et al.
10,188,851 B2 1/2019 Wenger et al.
10,441,776 B2 10/2019 Kirson et al.
10,779,875 B2 9/2020 Palti et al.
10,967,167 B2 4/2021 Hagemann et al.
11,103,698 B2 8/2021 Chang et al.
11,191,956 B2 12/2021 Giladi et al.
11,395,916 B2 7/2022 Wasserman et al.
11,654,279 B2 5/2023 Wasserman et al.
2004/0176804 A1 9/2004 Palti
2005/0209642 A1 9/2005 Palti
2006/0167499 A1 7/2006 Palti
2006/0276858 A1 12/2006 Palti
2007/0225766 A1 9/2007 Palti
2007/0239213 A1 10/2007 Palti
2009/0076366 A1 3/2009 Palti
2010/0324547 A1 12/2010 Palti
2011/0137229 A1 6/2011 Palti et al.
2012/0029419 A1 2/2012 Palti
2012/0283726 A1 11/2012 Palti
2014/0330268 A1 11/2014 Palti et al.
2017/0120041 A1 5/2017 Wenger et al.
2017/0209697 A1 7/2017 Wagner
2017/0215939 A1 8/2017 Palti et al.
2017/0281934 A1 10/2017 Giladi et al.
2018/0001075 A1 1/2018 Kirson et al.
2018/0001078 A1* 1/2018 Kirson ................ A61N 1/0492
2018/0008708 A1 1/2018 Giladi et al.
2018/0050200 A1 2/2018 Wasserman et al.
2018/0085575 A1 3/2018 Travers et al.
2018/0160933 A1 6/2018 Urman et al.
2018/0202991 A1 7/2018 Giladi et al.
2018/0280687 A1 10/2018 Carter et al.
2019/0117956 A1 4/2019 Wenger et al.
2019/0117963 A1 4/2019 Travers et al.
2019/0117970 A1 4/2019 Schmidt et al.
2019/0308016 A1 10/2019 Wenger et al.
2020/0001069 A1 1/2020 Kirson et al.
2020/0009376 A1 1/2020 Chang et al.
2020/0009377 A1 1/2020 Chang et al.
2020/0016067 A1 1/2020 Gotlib et al.
2020/0023179 A1 1/2020 Bomzon et al.
2020/0061360 A1 2/2020 Hagemann et al.
2020/0061361 A1 2/2020 Hagemann et al.
2020/0069937 A1 3/2020 Naveh et al.
2020/0078582 A1 3/2020 Alon et al.
2020/0108031 A1 4/2020 Borst et al.
2020/0114141 A1 4/2020 Bomzon et al.
2020/0114142 A1 4/2020 Bomzon et al.
2020/0121728 A1 4/2020 Wardak et al.
2020/0129761 A1 4/2020 Bomzon et al.
2020/0146586 A1 5/2020 Naveh et al.
2020/0155835 A1 5/2020 Wasserman et al.
2020/0171297 A1 6/2020 Kirson et al.
2020/0179512 A1 6/2020 Giladi et al.
2020/0219261 A1 7/2020 Shamir et al.
2020/0269037 A1 8/2020 Hagemann et al.
2020/0269041 A1 8/2020 Zeevi et al.
2020/0269042 A1 8/2020 Giladi et al.
2020/0368525 A1 11/2020 Maag et al.
2021/0031031 A1 2/2021 Wasserman et al.
2021/0038584 A1 2/2021 Voloshin-Sela
2021/0060334 A1* 3/2021 Avraham ............... G16H 50/50
2021/0069503 A1 3/2021 Tran et al.
2021/0138233 A1 5/2021 Deslauriers
2021/0162228 A1 6/2021 Urman et al.
2021/0177492 A1 6/2021 Travers et al.
2021/0187277 A1 6/2021 Wasserman et al.
2021/0196348 A1 7/2021 Wasserman
2021/0196967 A1 7/2021 Carlson et al.
2021/0199640 A1 7/2021 Patel et al.
2021/0202179 A1 7/2021 Saito et al.
2021/0203250 A1 7/2021 Wasserman et al.
2021/0268247 A1 9/2021 Story et al.
2021/0299439 A1 9/2021 Shamir et al.
2021/0299440 A1 9/2021 Deslauriers et al.
2021/0308446 A1 10/2021 Alon et al.
2021/0330950 A1 10/2021 Hagemann et al.
2021/0346694 A1 11/2021 Wasserman et al.
2021/0379362 A1 12/2021 Smith et al.
2021/0402179 A1 12/2021 Wasserman et al.
2021/0408383 A1 12/2021 Kalra et al.
2022/0088403 A1 3/2022 Voloshin-Sela et al.
2022/0095997 A1 3/2022 Wasserman
2022/0096821 A1 3/2022 Kirson et al.
2022/0096829 A1 3/2022 Farber et al.
2022/0118249 A1 4/2022 Bomzon et al.
2022/0161028 A1 5/2022 Giladi et al.
2022/0193435 A1 6/2022 Wasserman et al.
2022/0203111 A1 6/2022 Carlson et al.
2022/0267445 A1 8/2022 Tran et al.
2022/0280787 A1 9/2022 Bomzon et al.
2022/0288395 A1 9/2022 Voloshin-Sela et al.
2022/0313992 A1 10/2022 Wasserman
2022/0323753 A1 10/2022 Voloshin-Sela et al.
2022/0387784 A1 12/2022 Kirson et al.
2022/0409893 A1 12/2022 Wasserman et al.
2023/0019638 A1 1/2023 Wasserman
2023/0043071 A1 2/2023 Wasserman et al.
2023/0065587 A1 3/2023 Shnaiderman et al.
2023/0098801 A1 3/2023 Carlson
2023/0201616 A1 6/2023 Carlson
2024/0139505 A1 5/2024 Wasserman
2024/0149053 A1 5/2024 Kirson et al.
2024/0169536 A1 5/2024 Shamir et al.
2024/0207604 A1 6/2024 Deslauriers
2024/0216679 A1 7/2024 Wasserman et al.
2024/0216684 A1 7/2024 Wasserman et al.
2024/0216685 A1 7/2024 Wasserman et al.
2024/0219367 A1 7/2024 Wasserman et al.
2024/0238588 A1 7/2024 Bomzon et al.
2024/0325739 A1 10/2024 Wasserman et al.
2024/0325753 A1 10/2024 Levi
2024/0325768 A1 10/2024 Ben-Tov Kuperberg et al.
2024/0350799 A1 10/2024 Tran et al.
2025/0001194 A1 1/2025 Carlson
2025/0032041 A1 1/2025 Wasserman

* cited by examiner

| ROI | LAFI [V/cm amp.] |
| --- | --- |
| Optical tract and co. | 3.01 |
| Primary tumor C2-C5 | 2.85 |
| T2-T4 | 1.89 |

DELIVERING TUMOR TREATING FIELDS (TTFields) TO THE NECK, THORACIC SPINE, AND OPTIC TRACT

CROSS REFERENCE TO RELATED APPLICATIONS

This Application claims the benefit of U.S. Provisional Application 63/600,338, filed Nov. 17, 2023, which is incorporated herein by reference in its entirety.

BACKGROUND

Tumor Treating Fields (TTFields) therapy is a proven approach for treating tumors using alternating electric fields at frequencies between 50 kHz and 5 MHz (e.g., 100-300 kHz or 150-250 kHz). In the prior art Optune® system, TTFields are delivered to patients via two pairs of electrode assemblies (also called "transducer arrays") that are placed on the patient's skin near the tumor. The conventional approach is to position one pair of electrode assemblies to the left and right of the tumor, and to position the other pair of electrode assemblies anterior and posterior to the tumor. Each electrode assembly is connected via a multi-wire cable to an AC signal generator. The AC signal generator (a) sends an AC current through the anterior/posterior (A/P) pair of electrode assemblies for 1 second, which induces an electric field with a first direction through the tumor; then (b) sends an AC current through the left/right (L/R) pair of arrays for 1 second, which induces an electric field with a second direction through the tumor; then repeats steps (a) and (b) for the duration of the treatment. Each electrode assembly includes a plurality (e.g., between 9 and 30) of electrode elements.

SUMMARY OF THE INVENTION

One aspect of the invention is directed to a first method of treating one or more tumors in a subject's body located in at least one of (i) an upper half of the subject's thoracic spine, (ii) the subject's cervical spine, and (iii) the subject's head. The first method comprises (a) applying an alternating voltage between at least one first electrode element affixed to a left half of the subject's scalp and at least one second electrode element affixed to a right side of the subject's posterior thorax; (b) applying an alternating voltage between at least one third electrode element affixed to a right half of the subject's scalp and at least one fourth electrode element affixed to a left side of the subject's posterior thorax; and repeating step (a) and step (b) in an alternating sequence at least 10 times.

Some instances of the first method further comprise, prior to performing step (a) and step (b), affixing the at least one first electrode element to the left half of the subject's scalp; affixing the at least one second electrode element to the right side of the subject's posterior thorax; affixing the at least one third electrode element to the right half of the subject's scalp; and affixing the at least one fourth electrode element to the left side of the subject's posterior thorax.

In some instances of the first method, the at least one first electrode element, the at least one second electrode element, the at least one third electrode element, and the at least one fourth electrode element are capacitively coupled.

In some instances of the first method, the alternating voltage that is applied between the at least one first electrode element and the at least one second electrode element has a frequency between 100 kHz and 300 kHz, and the alternating voltage that is applied between the at least one third electrode element and the at least one fourth electrode element has a frequency between 100 kHz and 300 kHz.

In some instances of the first method, step (a) and step (b) are repeated in an alternating sequence at least 100 times.

In some instances of the first method, the one or more tumors comprise cancer cells located at the subject's C2-C5 vertebrae, cancer cells located at the subject's T2-T4 vertebrae, and cancer cells located in the subject's head. In some instances of the first method, the one or more tumors comprise at least one of cancer cells located at the subject's C2-C5 vertebrae, cancer cells located at the subject's T2-T4 vertebrae, and cancer cells located in the subject's head.

In some instances of the first method, the at least one first electrode element is affixed to an anterior portion of the left half of the subject's scalp, and the at least one third electrode element is affixed to an anterior portion of the right half of the subject's scalp. In some instances of the first method, the at least one second electrode element is affixed to an upper half of the right side of the subject's posterior thorax, and the at least one fourth electrode element is affixed to an upper half of the left side of the subject's posterior thorax.

In some instances of the first method, the at least one first electrode element is affixed to an anterior portion of the left half of the subject's scalp, and the at least one third electrode element is affixed to an anterior portion of the right half of the subject's scalp. And the at least one second electrode element is affixed to an upper half of the right side of the subject's posterior thorax, and the at least one fourth electrode element is affixed to an upper half of the left side of the subject's posterior thorax.

Another aspect of the invention is directed to a second method of treating one or more tumors in a subject's body located in at least one of (i) an upper half of the subject's thoracic spine, (ii) the subject's cervical spine, and (iii) the subject's optic tract. The second method comprises affixing at least one first electrode element to a left half of the subject's scalp; affixing at least one second electrode element to a right side of the subject's posterior thorax; affixing at least one third electrode element to a right half of the subject's scalp; affixing at least one fourth electrode element to a left side of the subject's posterior thorax; and repeating, in an alternating sequence (a) applying an alternating voltage between the at least one first electrode element and the at least one second electrode element, and (b) applying an alternating voltage between the at least one third electrode element and the at least one fourth electrode element. The repeating is performed after the affixing of the at least one first electrode element, the at least one second electrode element, the at least one third electrode element, and the at least one fourth electrode element.

In some instances of the second method, the at least one first electrode element, the at least one second electrode element, the at least one third electrode element, and the at least one fourth electrode element are capacitively coupled.

In some instances of the second method, the alternating voltage that is applied between the at least one first electrode element and the at least one second electrode element has a frequency between 100 kHz and 300 kHz, and the alternating voltage that is applied between the at least one third electrode element and the at least one fourth electrode element has a frequency between 100 kHz and 300 kHz.

In some instances of the second method, the at least one first electrode element comprises a plurality of electrode elements wired in parallel, the at least one second electrode element comprises a plurality of electrode elements wired in parallel, the at least one third electrode element comprises a plurality of electrode elements wired in parallel, and the at least one fourth electrode element comprises a plurality of electrode elements wired in parallel.

In some instances of the second method, the one or more tumors comprise cancer cells located at the subject's C2-C5 vertebrae, cancer cells located at the subject's T2-T4 vertebrae, and cancer cells located at the subject's optic tract. In some instances of the second method, the one or more tumors comprise at least one of cancer cells located at the subject's C2-C5 vertebrae, cancer cells located at the subject's T2-T4 vertebrae and cancer cells located at the subject's optic tract.

Another aspect of the invention is directed to a first apparatus for treating one or more tumors in a subject's body located in at least one of (i) an upper half of the subject's thoracic spine, (ii) the subject's cervical spine, and (iii) the subject's head. The first apparatus comprises at least one first electrode element affixed to a left half of the subject's scalp; at least one second electrode element affixed to a right side of the subject's posterior thorax; at least one third electrode element affixed to a right half of the subject's scalp; and at least one fourth electrode element affixed to a left side of the subject's posterior thorax.

In some embodiments of the first apparatus, the at least one first electrode element, the at least one second electrode element, the at least one third electrode element, and the at least one fourth electrode element are capacitively coupled.

BRIEF DESCRIPTION OF THE DRAWINGS

Various embodiments are described in detail below with reference to the accompanying drawings, wherein like reference numerals represent like elements.

DESCRIPTION OF THE PREFERRED EMBODIMENTS

Figure 1:
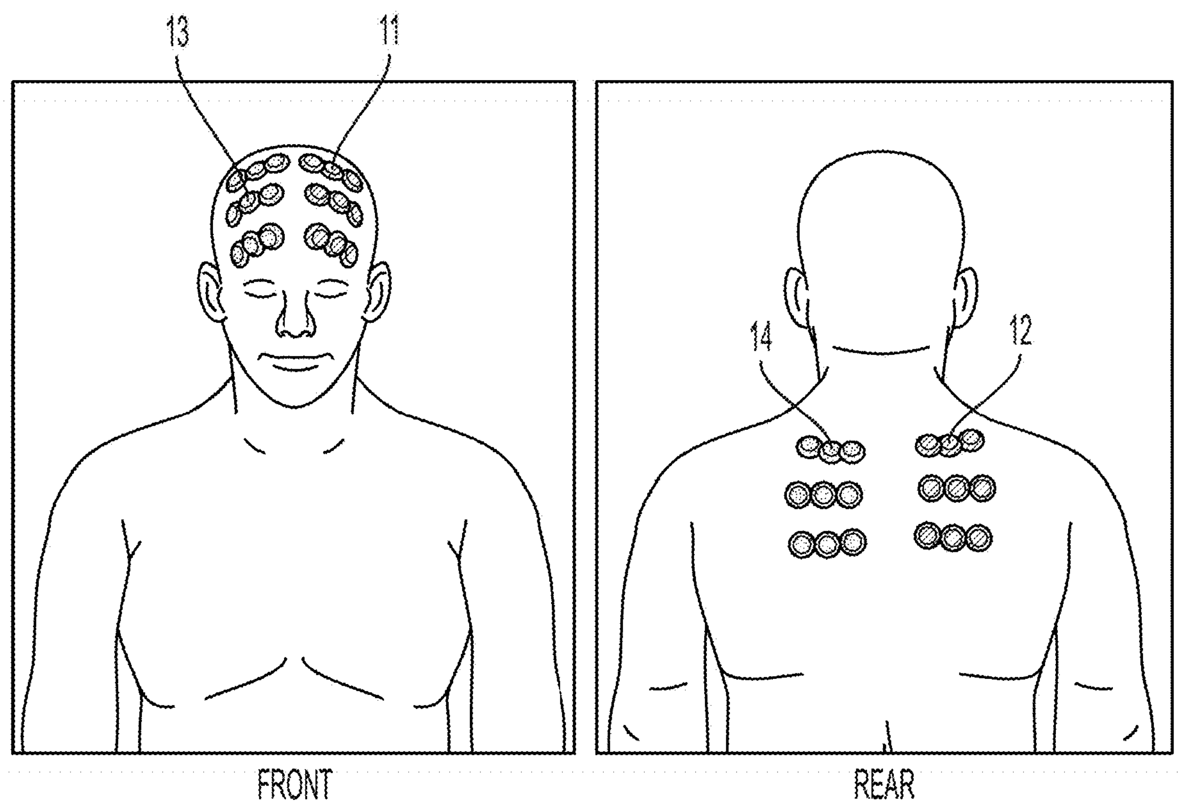
FIG. 1 depicts front and back views of positions where electrode assemblies should be positioned in order to treat tumors or metastases in the three regions of interest identified herein.

For TTFields to exert a therapeutic effect, field intensities should exceed a threshold of about 1 V/cm. When the tumor that is being treated is a localized within a single location, intensities of >1 V/cm can typically be achieved using the conventional positioning of the electrode assemblies described above. But when the cancer cells are distributed among two or more different locations within the subject's body, it may not be possible to achieve intensities of >1 V/cm in all those locations using the conventional positioning of the electrode assemblies.

One example of this situation occurred in a female patient with diffuse midline WHO grade IV glioma located at the C2-C5 vertebrae of the cervical spine, who was being treated with Optune® off-label for about a year, and whose condition was stable. But that patient's cancer metastasized into two opposite locations—one next the optical nerves (behind the left eye) and the other to the T2-T4 vertebrae of the spine. And the original positioning of the electrode assemblies did not yield sufficiently high field intensities at those two locations to treat those two metastases.

When faced with this problem, the inventor thought up a new way to arrange the electrode assemblies of a conventional Optune® system to induce TTFields with intensities above 1 V/cm in all three of the following regions of interest: (a) the C2-C5 vertebrae of the cervical spine, (b) the T2-T4 vertebrae of the thoracic spine, and (c) the optic tract behind the left eye. (These three regions of interest are collectively referred to herein as "the three ROIs.") This new arrangement positions four conventional 9-element Optune® electrode assemblies at the unconventional positions depicted in FIG. 1.

More specifically, in this new arrangement, a first electrode assembly 11 (which includes at least one first electrode element) is affixed to the left half of the subject's scalp (e.g., an anterior portion of the left half of the subject's scalp, above the left eyebrow) and a second electrode assembly 12 (which includes at least one second electrode element) is affixed to the right side of the subject's posterior thorax (e.g., the upper half of the right side of the subject's posterior thorax). A third electrode assembly 13 (which includes at least one third electrode element) is affixed to the right half of the subject's scalp (e.g., an anterior portion of the right half of the subject's scalp, above the right eyebrow) and a fourth electrode assembly 14 (which includes at least one fourth electrode element) is affixed to the left side of the subject's posterior thorax (e.g., the upper half of the left side of the subject's posterior thorax).

Then, one channel of the Optune® field generator applies an AC voltage between the electrode assembly 11 located on the left half of the subject's scalp (e.g., an anterior portion of the left half of the subject's scalp, above the left eyebrow) and the electrode assembly 12 located on the right side of the subject's posterior thorax (e.g., the upper half of the right side of the subject's posterior thorax); and the other channel of the Optune® field generator applies an AC voltage between the electrode assembly 13 located on the right half of the subject's scalp (e.g., an anterior portion of the right half of the subject's scalp, above the right eyebrow) and the electrode assembly 14 located on the left side of the subject's posterior thorax (e.g., the upper half of the left side of the subject's posterior thorax).

Figure 2:
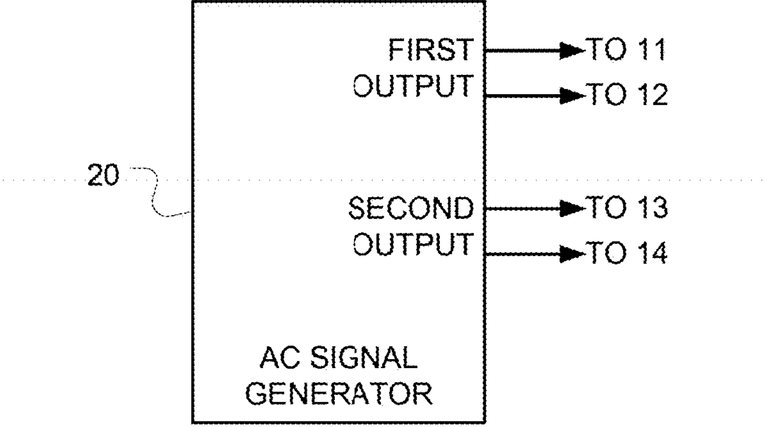
FIG. 2 is a block diagram of a system for driving the electrode assemblies depicted in FIG. 1 with AC voltage signals.

FIG. 2 is a block diagram of a system for driving the electrode assemblies 11-14 with AC voltage signals. The system includes an AC signal generator 20 that is designed to generate first and second AC outputs. When the system is used to apply TTFields to a person's body, the first AC output is applied across the first pair of electrode assemblies 11, 12; and the second AC output is applied across the second pair of electrode assemblies 13, 14.

When the AC signal generator 20 applies a voltage between electrode assemblies 11, 12, a first alternating electric field is induced in the subject's body. And when the AC signal generator 20 applies a voltage between electrode assemblies 13, 14, a second alternating electric field is induced in the subject's body. The voltage generated by the AC signal generator 20 in either case is preferably sufficient to induce an electric field of at least 1 V/cm (e.g., between 1 and 4 or between 1 and 10 V/cm) in all the relevant regions of interest.

As in the prior art Optune® system, (a) the first AC output is applied to the first pair electrode assemblies for an interval of time; (b) the second AC output is applied to the second pair of electrode assemblies for an interval of time; and the two-step sequence (a) and (b) is repeated (e.g., at least 10 times, at least 100 times, or at least 1000 times) for the duration of the treatment. But the positioning of the electrode assemblies (depicted in FIG. 1) differs from the conventional positioning used for the Optune® electrode assemblies.

Simulations were performed to determine the field strengths in the three ROIs for the electrode assembly positioning depicted in FIG. 1 using the following parameters for the simulation: Operating frequency of the AC signal generator 20: 200 kHz; Simulation platform: Sim4Life Ver. 6.2.1.4910; Models used: Ella; Array model: INE; Parameter files: Per PHYS0010; Field normalization: 1 Amp/Isim; and Grid/Mesh properties: arrays—0.75 mm, body—1 mm.

Figure 3:
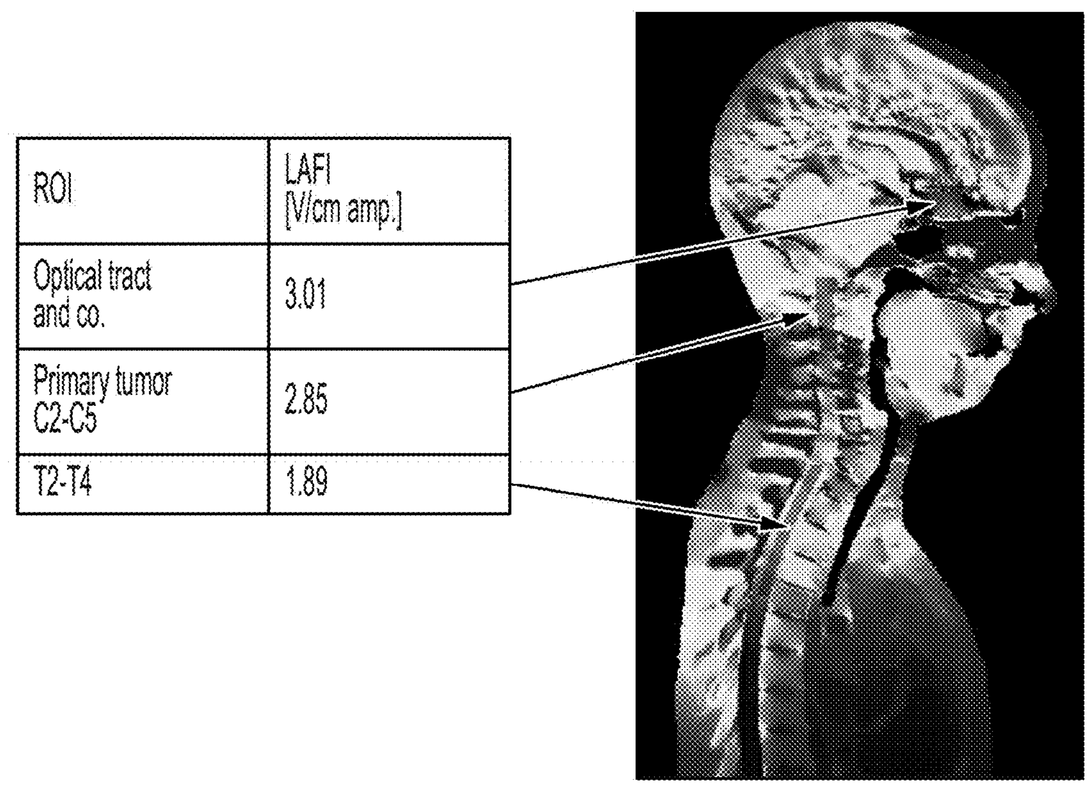
FIG. 3 is a map of the field intensities that were obtained in the regions of interest using the FIG. 1 layout for the electrode assemblies.

FIG. 3 shows the results of the simulations. More specifically, the field intensity was 3.01 V/cm at the optical tract, 2.85 V/cm at C2-C5, and 1.89 V/cm at T2-T4. The simulated resistance was 149.7 Ohms in the first channel and 147.2 Ohms in the second channel. This shows that the layout depicted in FIG. 1 for the electrode assemblies 11-14 can be used to deliver TTFields at therapeutically effective levels (i.e., greater than 1 V/cm) in all three of the ROIs identified above. It also shows that applying AC voltages across electrode assemblies positioned as described herein can yield intensities that are >1 V/cm in locations that are distributed throughout (i) an upper half of the subject's thoracic spine, (ii) the subject's cervical spine, and (iii) the subject's head (e.g., in the subject's optic tract).

Note that for the positioning and simulations described above in connection with FIGS. 1-3, each of the electrode assemblies 11-14 was configured as an array of 9 individual electrode element discs. But in alternative embodiments, each electrode assembly may include a different number (e.g., between 2 and 25) of electrode elements. For example, a given electrode assembly may be configured as a 2×2 array of individual electrode elements. In other alternative embodiments, a given set of electrode elements may include only a single electrode element (which may be any suitable shape including but not limited to round and rectangular). Note also that in the embodiments described herein, all the electrode assemblies 11-14 have the same number of electrode elements. But in alternative embodiments, the number of electrode elements on the scalp and thorax electrode assemblies could be different (e.g., 9 electrode elements on the scalp arrays and 13 electrode elements on the thorax arrays).

Conventional 9-element Optune® electrode assemblies were used for the positioning and simulations described above. After the electrode assemblies 11-14 are positioned on the subject's body, the following steps are repeated in an alternating sequence: (a) applying an alternating voltage between the first set of electrode elements 11 and the second set of electrode elements 12, and (b) applying an alternating voltage between the third set of electrode elements 13 and the fourth set of electrode elements 14. In some embodiments, the frequency of these alternating voltages is between 100 kHz and 300 kHz (e.g., 200 kHz). In other embodiments, the frequency of these alternating voltages could be between 50 kHz and 5 MHz, 50 kHz-1 MHz, 50-500 kHz, 75-300 kHz, or 150-250 kHz.

The electrode assemblies 11-14 can have a flexible backing that is configured for affixation to a subject's body. Suitable materials for the flexible backing include cloth, foam, and flexible plastic (e.g., similar to corresponding materials used in bandages). A plurality of capacitively coupled electrode elements are positioned on the inner side of the flexible backing, and each of the capacitively coupled electrode elements has a conductive plate with a dielectric layer disposed thereon that faces inward. Optionally, temperature sensors (e.g., thermistors) may be positioned beneath each of the electrode elements in a manner that is similar to the conventional arrangement used in the Novocure Optune® system. A set of conductors connects to the conductive plates of each of the plurality of capacitively coupled electrode elements. The conductors may be implemented using, for example, discrete wiring or using traces on a flex circuit. A layer of adhesive is configured to hold portions of the flexible backing that are not covered by any of the electrode elements against the subject's body.

Alternative constructions for the electrode assemblies may also be used, including, for example, electrode assemblies that use ceramic elements that are not disc-shaped, and electrode assemblies that use non-ceramic dielectric materials positioned over a plurality of flat conductors. Examples of the latter include polymer films disposed over pads on a printed circuit board or over flat pieces of metal.

Electrode assemblies that use electrode elements that are not capacitively coupled may also be used. In this situation, each element of the electrode assembly would be implemented using a region of a conductive material (e.g., a layer of graphite) that is configured for placement against a subject's body, with no insulating dielectric layer disposed between the conductive elements and the body. Other alternative constructions for implementing the electrode assemblies may also be used, as long as they are (a) capable of delivering TTFields to the subject's body and (b) positioned in the locations specified herein. Optionally, a layer of conductive hydrogel or conductive adhesive may be disposed between the electrode assemblies and the subject's body in any of the embodiments described herein.

In the configuration depicted in FIG. 1, all of the electrode assemblies 11-14 are oriented in a portrait orientation (as opposed to a landscape orientation). But in alternative arrangements, one or more of the electrode assemblies 11-14 could be shifted to a landscape orientation.

It is important to note that the positions of the electrode assemblies (and/or the elements within each of those arrays) may be varied from the exact locations depicted in FIG. 1, as long as the movement is small enough so that the respective anatomic description above remains unchanged. For example, the electrode elements positioned on the scalp in FIG. 1 can move up, down, or to either side, as long as they remain positioned on the respective side of the subject's scalp. Similarly, the electrode elements positioned on the posterior thorax in FIG. 1 can move up, down, or to either side, as long as they remain on the respective side of the posterior thorax.

Within this limited range of movement, the optimum position of each of the electrode assemblies may be determined using simulations (e.g., finite element simulations) for each individual subject to calculate the resulting electric field for each combination of positions for the electrode assemblies, and selecting the combination that provides the best results (e.g., the highest percentage of the ROI with an intensity above 1 V/cm). An indication of the selected combination can then be output to the care provider using, for example, a suitable display or printout. The care provider can then apply the electrode assemblies to the subject at the positions indicated by the output, hook the sets of electrode elements up to an AC signal generator, and commence TTFields treatment.

It is expected that lowering the position of the two electrode assemblies 12, 14 located on the subject's posterior thorax will increase the field strength between T2 and T4. But simulations have not yet been run to confirm that expectation.

In some embodiments, each of the electrode assemblies (i.e., the first, second, third, and fourth electrode assemblies) each include only a single electrode element. In other embodiments, each of the electrode assemblies (i.e., the first, second, third, and fourth electrode assemblies) include two or more electrode elements. In the latter embodiments, all of the electrode elements within any given one of the electrode assemblies can be wired in parallel.

Advantageously, the layouts described herein can be used to deliver TTFields at therapeutically effective levels (i.e., greater than 1 V/cm) to all three ROIs. Furthermore, use of the layouts described herein is not limited to treating one or more tumors in a subject's body located in at least one of (i) an upper half of the subject's thoracic spine, (ii) the subject's cervical spine, and (iii) the subject's optic tract. To the contrary, the layouts described herein can be used to treat one or more tumors in a subject's body located in at least one of (i) an upper half of the subject's thoracic spine, (ii) the subject's cervical spine, and (iii) parts of the subject's head other than the optic tract.

Finally, while the embodiments described herein depict electrode assemblies positioned on the surface of the subject's skin, the electrode assemblies or a subset thereof may also be implanted beneath the surface of the subject's skin.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method of treating one or more tumors in a subject's body located in at least one of
- (i) an upper half of the subject's thoracic spine,
- (ii) the subject's cervical spine, and
- (iii) the subject's head, the method comprising:
- (a) applying an alternating voltage between at least one first electrode element affixed to a left half of the subject's scalp and at least one second electrode element affixed to a right side of the subject's posterior thorax;
- (b) applying an alternating voltage between at least one third electrode element affixed to a right half of the subject's scalp and at least one fourth electrode element affixed to a left side of the subject's posterior thorax; and
- repeating step (a) and step (b) in an alternating sequence at least 10 times.

2. The method of claim 1, further comprising, prior to performing step (a) and step (b):
- affixing the at least one first electrode element to the left half of the subject's scalp;
- affixing the at least one second electrode element to the right side of the subject's posterior thorax;
- affixing the at least one third electrode element to the right half of the subject's scalp; and
- affixing the at least one fourth electrode element to the left side of the subject's posterior thorax.

3. The method of claim 1, wherein the at least one first electrode element, the at least one second electrode element, the at least one third electrode element, and the at least one fourth electrode element are capacitively coupled.

4. The method of claim 1, wherein the alternating voltage that is applied between the at least one first electrode element and the at least one second electrode element has a frequency between 100 kHz and 300 kHz, and wherein the alternating voltage that is applied between the at least one third electrode element and the at least one fourth electrode element has a frequency between 100 kHz and 300 kHz.

5. The method of claim 1, wherein step (a) and step (b) are repeated in an alternating sequence at least 100 times.

6. The method of claim 1, wherein the one or more tumors comprise cancer cells located at the subject's C2-C5 vertebrae, cancer cells located at the subject's T2-T4 vertebrae, and cancer cells located in the subject's head.

7. The method of claim 1, wherein the one or more tumors comprise at least one of cancer cells located at the subject's C2-C5 vertebrae, cancer cells located at the subject's T2-T4 vertebrae, and cancer cells located in the subject's head.

8. The method of claim 1, wherein the at least one first electrode element is affixed to an anterior portion of the left half of the subject's scalp, and the at least one third electrode element is affixed to an anterior portion of the right half of the subject's scalp.

9. The method of claim 1, wherein the at least one second electrode element is affixed to an upper half of the right side of the subject's posterior thorax, and the at least one fourth electrode element is affixed to an upper half of the left side of the subject's posterior thorax.

10. The method of claim 1, wherein the at least one first electrode element is affixed to an anterior portion of the left half of the subject's scalp, and the at least one third electrode element is affixed to an anterior portion of the right half of the subject's scalp, and
- wherein the at least one second electrode element is affixed to an upper half of the right side of the subject's posterior thorax, and the at least one fourth electrode element is affixed to an upper half of the left side of the subject's posterior thorax.

11. A method of treating one or more tumors in a subject's body located in at least one of
- (i) an upper half of the subject's thoracic spine,
- (ii) the subject's cervical spine, and
- (iii) the subject's optic tract, the method comprising:
- affixing at least one first electrode element to a left half of the subject's scalp;
- affixing at least one second electrode element to a right side of the subject's posterior thorax;
- affixing at least one third electrode element to a right half of the subject's scalp;
- affixing at least one fourth electrode element to a left side of the subject's posterior thorax; and
- repeating, in an alternating sequence (a) applying an alternating voltage between the at least one first electrode element and the at least one second electrode element, and (b) applying an alternating voltage between the at least one third electrode element and the at least one fourth electrode element,
- wherein the repeating is performed after the affixing of the at least one first electrode element, the at least one second electrode element, the at least one third electrode element, and the at least one fourth electrode element.

12. The method of claim 11, wherein the at least one first electrode element, the at least one second electrode element, the at least one third electrode element, and the at least one fourth electrode element are capacitively coupled.

13. The method of claim 11, wherein the alternating voltage that is applied between the at least one first electrode element and the at least one second electrode element has a frequency between 100 kHz and 300 kHz, and wherein the alternating voltage that is applied between the at least one third electrode element and the at least one fourth electrode element has a frequency between 100 kHz and 300 kHz.

14. The method of claim 11, wherein the at least one first electrode element comprises a plurality of electrode elements wired in parallel, the at least one second electrode element comprises a plurality of electrode elements wired in parallel, the at least one third electrode element comprises a plurality of electrode elements wired in parallel, and the at least one fourth electrode element comprises a plurality of electrode elements wired in parallel.

15. The method of claim 11, wherein the one or more tumors comprise cancer cells located at the subject's C2-C5 vertebrae, cancer cells located at the subject's T2-T4 vertebrae, and cancer cells located at the subject's optic tract.

16. The method of claim 11, wherein the one or more tumors comprise at least one of cancer cells located at the subject's C2-C5 vertebrae, cancer cells located at the subject's T2-T4 vertebrae and cancer cells located at the subject's optic tract.

* * * * *